Figure 1:
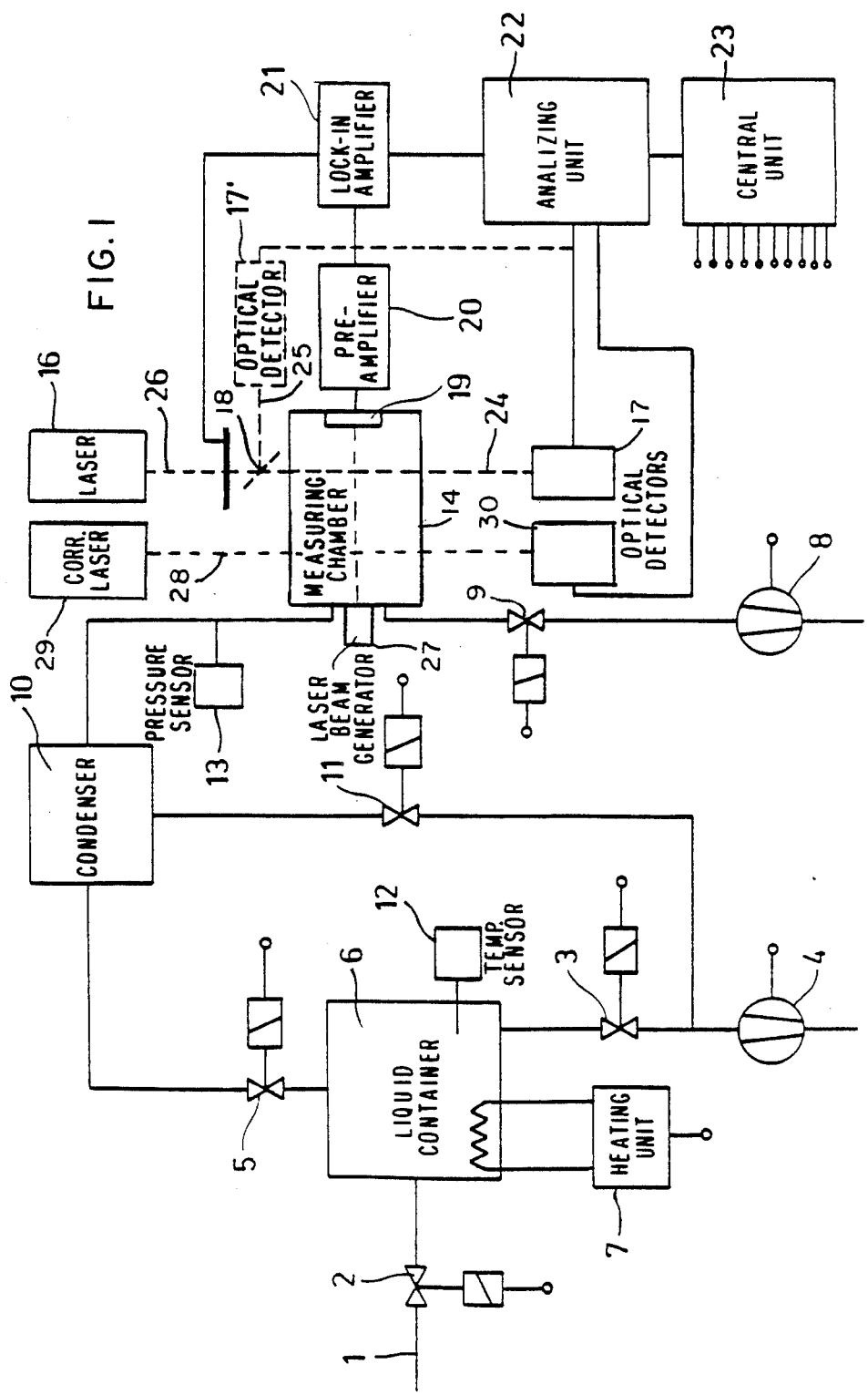

United States Patent [19]

Michaelis et al.

[11] Patent Number: 4,943,161
[45] Date of Patent: Jul. 24, 1990

[54] METHOD AND APPARATUS FOR THE DETECTION OF HYDROCARBONS DISSOLVED IN BODIES OF WATER

[75] Inventors: Walfried Michaelis, Seevetal; Claus Weitkamp, Wentorf, both of Fed. Rep. of Germany

[73] Assignee: Gkss Forschungszentrum Geesthacht GmbH, Geesthacht, Fed. Rep. of Germany

[21] Appl. No.: 277,183

[22] Filed: Nov. 29, 1988

Related U.S. Application Data

[63] Continuation-in-part of Ser. No. 573,876, Jan. 25, 1984, abandoned.

[30] Foreign Application Priority Data

Jan. 27, 1983 [DE] Fed. Rep. of Germany ....... 3302656

[51] Int. Cl.$^5$ ............................................. G01N 21/00
[52] U.S. Cl. .................................. 356/437; 356/432; 250/301; 436/29
[58] Field of Search ............. 356/51, 402, 407, 432 T, 356/437, 72, 73; 250/301, 304, 343, 345; 436/28, 29, 30, 32

[56] References Cited

U.S. PATENT DOCUMENTS

| | | | |
|---|---|---|---|
| 2,694,923 | 11/1954 | Carpenter | 250/343 X |
| 2,918,579 | 12/1959 | Slobod et al. | 250/301 X |
| 3,455,144 | 7/1969 | Bradley | 436/29 X |
| 4,051,372 | 9/1977 | Aine | 436/29 X |
| 4,105,919 | 8/1978 | Bridges et al. | 250/341 |
| 4,394,573 | 7/1983 | Correa et al. | 250/301 |
| 4,492,862 | 1/1985 | Grynberg et al. | 250/343 X |

FOREIGN PATENT DOCUMENTS 1431269 4/1976 United Kingdom ................ 250/343

OTHER PUBLICATIONS

Bruce et al., *Applied Optics*, vol. 15, No. 12, Dec. 1976, pp. 2970-2972.
McClelland, *Optics News*, Winter 1979, pp. 18-23.
Herrmann et al., *IBM Technical Disclosure Bulletin*, vol. 21, No. 10, Mar. 1979, pp. 4208-4209.
Herrmann et al., *Infrared Physics*, vol. 19, No. 3-4, Aug. 1979, pp. 455-459.
Jackson et al., *Applied Optics*, vol. 20, No. 8, Apr. 15, 1981, pp. 1333-1344.

*Primary Examiner*—F. L. Evans

[57] ABSTRACT

A method and apparatus for the detection of hydrocarbons dissolved in bodies of water and for the determination of their concentration in the water wherein a water sample is introduced into a sealed system in which the hydrocarbons are driven out of solution into a gas phase by heating the sample or exposing it to low pressure, or both, a laser beam of a wavelength or a frequency which provides for at least partial overlapping with the absorption lines of the hydrocarbons is directed through the gaseous phase, a correction laser beam of a wavelength such that it is not subjected to absorption by hydrocarbons is also directed through the gaseous phase to determine the influence of gases other than hydrocarbons and the amount of hydrocarbons in the water iscalculated from the amount of light energy absorbed in the gas phase by any hydrocarbons therein and a correction as determined by the correction laser beam.

9 Claims, 2 Drawing Sheets

METHOD AND APPARATUS FOR THE DETECTION OF HYDROCARBONS DISSOLVED IN BODIES OF WATER

This is a continuation-in-part application of application Ser. No. 573,876, filed Jan. 25, 1984, now abandoned.

BACKGROUND OF THE INVENTION

The invention resides in a method and apparatus for the detection of hydrocarbons dissolved in bodies of water and a determination of the concentration of the hydrocarbons in the water.

Detection and quantitative determination of hydrocarbons dissolved in liquids, particularly in water such as ground water and seawater, is of great practical importance in many technical areas. This is true for applications in the laboratory as well as in nature. Survey for leakage of gas and crude oil pipelines in the sea is an example of the latter type. Leakage of pipelines and of crude oil deposits will result, among others, in the presence in the seawater of volatile hydrocarbons, of which mostly aliphatic compounds, especially methane, are utilized in the process of determining hydrocarbon presence. In this connection, methods and apparatus suitable for use in connection with remotely controlled operation or fully automatic operation, which permit installation in a remote apparatus carrier and permit continuous or quasi-continuous in-situ measurements, are of particular interest. The presently performed methods of taking water samples from on board a ship and subjecting the samples subsequently to laboratory tests for the determination of methane content in the usual manner does not fulfill the needs.

There is also known (from U.S. Pat. No. 3,436,188) a method, which, in principle, appears to be suitable for in-situ detection of the presence of aliphatic hydrocarbons in water. This method is based on the application of ultrasonic cavitation which results in the formation of hydrogen and hydroxyl ions and the reaction of the hydroxyl ions so formed with any aliphatic hydrocarbons that might be present. In this method there are finally formed aldehydes or ketones which may be determined colorimetrically. The detection, however, is limited to 100 ppm (100:10$^6$) so that very small concentrations go unnoticed.

It is the object of the present invention to provide a method and apparatus which permits detection and quantitative determination of volatile hydrocarbons in any type of liquid with a detection sensitivity which is greater by orders of magnitudes, that is, in which the sensitivity limits are in some variations in the ppb range (1:10$^9$).

SUMMARY OF THE INVENTION

In order to detect and measure hydrocarbons dissolved in water, water is introduced in a sealed system wherein it is heated or exposed to vacuum or both so that any hydrocarbons are driven out of solution into a gas phase through which a first laser beam of a light wavelength which provides for at least partial overlapping with the absorption lines of the hydrocarbons is directed. In the gas phase, laser light energy is absorbed at a rate which is measured and which is proportional to the concentration of hydrocarbons in the gas phase and the concentration of hydrocarbons in the water sample is then accurately calculated from the concentration of the hydrocarbons in the gas phase. Since other gases which are of no interest but which affect the measurement of hydrocarbons are generally present in the gas sample, a reference laser beam is directed through the gaseous phase which has a wavelength at which it is not subject to absorption by hydrocarbons so that if absorption caused by such other gases to permit determination of the influence of those other gases and by comparison disregard of the effect of those other gases on the measurement results of the first beam. Even very small amounts of hydrocarbons can be detected by this technique quite accurately.

For the detection and determination of hydrocarbons in a liquid, the liquid is sampled continuously or batchwise, whereupon the pressure of the samples is reduced and/or their temperature is increased so that the hydrocarbons contained therein are, at least partially, transferred into the gaseous phase which, directly above the liquid or in a suitable analyzer chamber, is quantitatively analyzed by means of absorption or laser light so as to determine the compounds having the molecules to be detected. These molecules have absorption lines to which the laser light is tuned.

The invention is described in greater detail on the basis of an example—methane dissolved in water—but it is applicable to all liquids capable of dissolving hydrocarbons. Compounds to be detected are, of course, not only methane but any compound which has one or more frequency ranges within the ultraviolet, the visible or the infrared range in which certain electromagnetic radiation is measurably absorbed.

In accordance with the law of mass action, the distribution equilibrium between the gas phase and the gases in solution is given by:

$$\frac{P_I}{[X]_{II}} = H = \text{constant}$$

wherein $P_I$ is the partial pressure of the gas and $[X]_{II}$ is the concentration of the gases dissolved in the liquid phase. The ratio of both values is determined by the temperature-dependent Henry constant H. For example, with methane in water, the Henry constants are:

$$\text{at } 0° \text{ C.} \quad H = 2.2 \times 10^4 \frac{\text{atm}}{\text{mole ratio}}$$

and $$\text{at } 90° \text{ C.} \quad H = 7.1 \times 10^4 \frac{\text{atm}}{\text{mole ratio}}$$

It is apparent, therefore, that, by reducing the pressure of the water sample or by increasing its temperature or both, the volatile compounds dissolved in the water may be caused to be released at least to a large extent.

The partial pressure of the volatile compound is determined in accordance with the invention by sensing absorption of laser light which is directed through the gas volume directly above the surface of the liquid or in a separate test chamber either continuously, or in a pulsed or chopped fashion. In the latter case, the gaseous phase is exposed to a condenser so as to remove, from the gases, vapors if the liquid is of the type which itself is noticeably volatile. In addition to providing mechanical advantages, this method is preferred since it avoids undesired absorption of laser light by vapors of the carrier liquid. In some cases, such absorption may have a detrimental effect on the measuring results.

If a laser beam of an intensity $I_o$ penetrates a gas volume for a distance $l$ wherein the volatile compound to be detected is present at a partial pressure of $P_I$, the laser beam will be attenuated (absorbed) by the factor $$\frac{I}{I_o} = e^{-P_I \alpha l}$$

wherein $\alpha$ is the absorption coefficient of the particular gas. The light intensity transmitted is measured by a light sensitive detector which, depending on the frequency range and the light intensity utilized, consists of a photomultiplier and a solid-state diode. Since the penetration distance $l$ and, at a given gas pressure, also the coefficient $\alpha$ are known, the measured attenuation of the laser beam permits determination of the partial pressure $P_I$ and, as a result, of the content of hydrocarbons dissolved in the liquid. If the laser output intensity $I_o$ is not known or is not constant at times, it may be determined with the aid of a second detector utilizing either a beam splitter in front of the test chamber, the diffuse reflection at the chamber entrance window, or other components. The wavelength of the laser is so selected that the coefficient $\alpha$ achieves the highest possible value, that is, the emission line of the laser should correspond as much as possible to the absorption line of the gasses to be measured. Since the width of the absorption line depends on the total gas pressure, adjusting suitably the pressure in the test chamber permits optimizing of the coefficient $\alpha$. With the aid of two or more mirrors, multiple laser beam reflection can be achieved so that the absorption distance or length $l$ is increased and the sensitivity is improved. Since generally several volatile compounds are present in the gas phase, undesired sensitivity is excluded by additional use of a second correction laser beam of a frequency different from that of the first laser beam as a reference.

An alternative possibility for the detection of gases and their quantitative determination resides in a method wherein the measurement signal is obtained by means of an acoustic detector instead of an optical detector. This is possible because absorption of laser light in gas results in partial or complete conversion of the energy absorbed in the chamber into heat, which, if the light intensity is modulated, causes pressure variations in the gas volume at the modulation frequency. These pressure vibrations correspond to, or actually are, acoustic vibrations which may be picked up by a sensitive microphone. For high sensitivity, it is advantageous to utilize the resonance frequency of the opto-acoustic cells. In this embodiment, the absorption distance $l$ may also be increased by the provision of a number of mirrors so that also the detection capabilities are increased. The power output of the laser may be normalized, if necessary, by means of optical detection of the beam or by means of a beam guide or utilization of diffuse reflection.

For determining the rate of absorption of the laser beam, the local changes of the index of refraction which are caused by light absorption and the resulting energy transfer into heat are utilized. A test laser beam of the same or a different wavelength but sufficiently strong that it penetrates the gas experiences a refraction which is proportional to the partial pressure of the gas to be detected and which can be determined by a position sensitive detector. With this photothermic deflection of the test beam, high detection sensitivity and normalization is obtained similar to those as described in the alternative methods.

As light source, any lasers may be utilized which, either—as in the case of lasers with predetermined frequency—incidentally coincide completely or partially with the absorption line or some absorption lines of a hydrocarbon to be detected or which—in the case of frequency-adjustable lasers—may be tuned to one or more absorption lines of such hydrocarbon. Preferred are gas or diode lasers. Among gas lasers, hydrocarbon fluoride or deuterium fluoride lasers are advantageous since they have an emission spectrum (2.5–4.1 $\mu$m) which includes several lines that are absorbed by aliphatic and aromatic hydrocarbons, or a helium-neon laser whose long-wave line at 3.39 $\mu$m, for example, is absorbed by methane with a highly effective cross section, that is, at a high rate. If the incidental overlapping of the absorption lines of the compounds to be detected with lasers of predetermined frequency is only partial, the absorption in the sample gas may be increased by the application of a magnetic field to the excited laser gas or to the sample gas phase which results in a splitting and transformation of the absorption line. Variable diode lasers may be adjusted to maximum absorption by changing pressure, temperature, magnetic field and diode energization. As adjustable lasers, also color-centered lasers may be considered for use.

SHORT DESCRIPTION OF THE DRAWINGS

Figure 2:
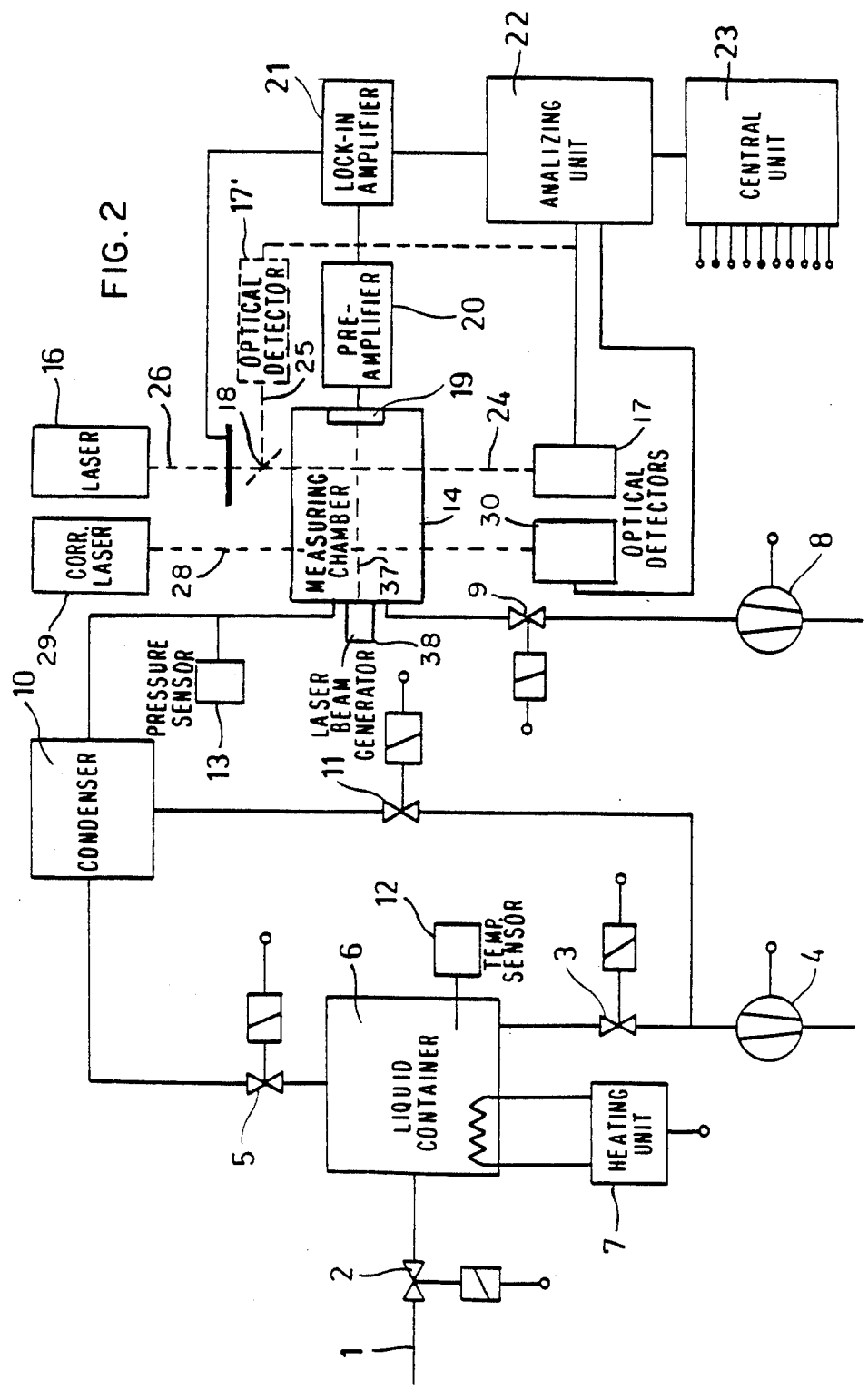

FIG. 1 is presented to facilitate understanding of the invention on the basis of a particular embodiment; and FIG. 2 shows the same arrangement, however with a laser beam utilized to measure the amount of hydrocarbon present.

EXEMPLARY DESCRIPTION OF THE INVENTION

As shown in FIG. 1, the liquid to be tested or a part thereof is supplied to the container 6 from admission line 1 under the control of valve 2 or by means of a pump 4 through open valve 3 with valve 5 closed. After valves 2 and 3 are closed, hydrocarbons dissolved in the liquid are driven fully or partially out of solution by means of the heater 7 or by a reduction of pressure by means of pump 8 which produces a vacuum by way of valves 5 and 9 or both. Vapors generated from the liquid in the process are condensed in the condenser 10. Any condensate generated in the condenser 10 may be removed by pump 4 when valve 11 is opened. Temperature and pressure can be controlled with the aid of the thermometer 12 and the pressure gauge 13. A portion of the gases reaches measuring chamber 14 in which light 26 of a laser 16, which is modulated by a mechanical interrupter (chopper) 15, is partially absorbed by any hydrocarbons to be detected. An optical reference detector 17 which is disposed in the laser beam path 24 serves to normalize the system depending on the output intensity of the laser 16. Alternatively, a beam splitter 18 may be arranged in front of the measuring chamber 14 such that a split section of the beam is directed to a detector 17'. The acoustic signal generated in the gas by the absorption of light is received by a sensitive microphone 19 and is amplified in a preamplifier 20 and then supplied to a lock-in amplifier 21. This amplifier 21 receives a reference signal from the interrupter 15. The sensitivity may be increased by providing adjacent the measuring chamber 14 magnetic field generating means 27 for generating in the measuring chamber 14 a magnetic field which optimizes overlapping of the laser beam emission spectrum and the hydrocarbon absorption spectrum. It is pointed out however that not only hydrocarbons but also other gases, especially water vapors, are driven out of solution together with the hydrocarbons. Inasmuch as such other gases are not of environmental concern they do not need to be detected but they may will cause absorption of the laser beam and therefore falsify the measurement. A correction laser beam 28 of a laser source 29 which is preferably not subject to absorption by hydrocarbons but subject to absorption by those other gases, especially water vapors, is therefore directed through the gas sample chamber 14 and its intensity loss is measured in an optical detector 30 as an indication of the influence of such other gases on the measurement result for hydrocarbons. As analyzing unit 22 generates a ratio of the output signal of the lock-in amplifier 21 and the reference detector 17 and analyzes this ratio, taking into consideration the values supplied by the sensors 12 and 13 (temperature and pressure). It also deducts the contribution to the test result of gases other than hydrocarbons, especially water vapors, as determined by the intensity loss of the correction laser beam. A control unit 23 controls the measuring procedure and, especially, operates the pumps 4, 8 and the valves 2, 5, 9, 11 in the proper sequence. After completion of the measuring procedure, the sample gas is removed by means of the pump 8, the container 6 is emptied by means of the pump 4 and a new liquid sample is introduced. Sampling and measuring may be performed alternately in fast shifts so as to provide for a quasi-continuous hydrocarbon detecting and measuring process.

As shown in FIG. 2 a laser beam generator 38 is disposed at one side of the measuring chamber 14 directing a laser beam 37 through the chamber 14 to a laser beam position sensor 39 disposed at the other side to determine deflection of the laser beam as caused by the change of index of refraction as a result of absorption of the first laser beam by hydrocarbons in the gas phase.

With the method according to the invention, incorrect measurement results as they may be generated by compounds other than the hydrocarbons to be detected may be eliminated by comparison with the absorption results of the correction laser beam which is also directed through the gas phase but has a wavelength at which the laser light is subject to little absorption by the hydrocarbons to be detected but rather by other gases, especially water vapors, for high selectivity and high accuracy.

All the equipment may be disposed in a submersible carrier for the survey of undersea gas and crude oil for leakages and for the discovery of undersea gas and crude oil deposits. Alternatively, the equipment may be disposed on board a ship which has a downwardly extending suction line through which sample water to be tested is gathered.

What is claimed is:

1. A method for the detection and the measurement of hydrocarbons dissolved in bodies of water, comprising the steps of: introducing a water sample, without a loss of hydrocarbons therefrom, into a sealed measuring system, driving any hydrocarbons out of solution in the water sample into a gaseous phase, directing a first laser beam of a wavelength selected so as to provide for at least partial overlapping with the absorption lines of said hydrocarbons through said gaseous phase for absorption therein by hydrocarbons, directing a correction laser beam of a wavelength at which such correction beam is not subject to absorption by the hydrocarbons through said gaseous phase so as to determine the contribution of gases other than hydrocarbons to the absorption of said first laser beam, determining the absorption of said first laser beam by said hydrocarbons, calculating the partial pressure of said hydrocarbons in said gaseous phase from the absorption of said first laser beam in said gaseous phase by the hydrocarbons, and determining the concentration of the hydrocarbons in the water sample from the partial pressure of the hydrocarbons in the gaseous phase on the basis of the distribution equilibrium of the hydrocarbons utilizing the given temperature and pressure conditions.

2. A method according to claim 1, wherein said partial pressure is determined at a given beam path length in said gaseous phase and at a given total pressure by measuring the attenuation of the first laser beam in the gaseous phase.

3. A method according to claim 1, wherein, for determining said partial pressure, the first laser beam intensity is modulated so as to cause heat generation in said gaseous phase by absorption of the first laser beam at a rate which is in accordance with the modulation frequency, and which causes pressure variations that are detected by an acoustic detector.

4. A method according to claim 1, wherein for determining the partial pressure, local changes in the refraction index in the gas phase which are caused by partial absorption of the first laser beam and which are proportional to the partial pressure of hydrocarbons in the gas phase are measured by directing a second laser beam through said gas phase and determining its deflection in said gas phase.

5. A method according to claim 1, wherein the beam length of said first laser beam in said gas phase is increased by reflecting the beam at least once back through the gas phase so as to increase its absorption and the detection capabilities.

6. A method according to claim 1, wherein said hydrocarbons are driven out of solution by increasing the temperature of said sample.

7. A method according to claim 1, wherein said hydrocarbons are driven out of solution by reducing the pressure in said measuring system.

8. A method according to claim 1, wherein a magnetic field is generated within said gaseous phase so as to influence the first laser beam or the sample gas for optimizing overlapping of the first laser beam emission spectrum and the absorption spectrum of the hydrocarbons to be detected.

9. An apparatus for the detection and the measurement of hydrocarbons dissolved in bodies of water, said apparatus comprising: a sealed measuring system, a container for the reception of water samples in said sealed measuring system, heating means for heating said sample and evacuation means for reducing the pressure in said container for driving any hydrocarbons out of said sample into a gas phase, a chamber for receiving said gas phase, means for sensing the temperature and means for sensing the pressure in said chamber, a laser beam source so associated with said system as to provide a laser beam which extends through said gas phase, said laser source being selected so as to provide light with a wavelength providing for at least partial overlapping with the absorption lines of the hydrocarbons to be detected to thereby cause substantial attenuation of said laser beam, means for measuring the attenuation of said laser beam, a correction laser beam source also associated with said system so as to provide a beam which extends through said gas phase, said correction beam having a wavelength at which such correction beam is not subject to absorption by the hydrocarbons through said gaseous phase so as to determine the contribution of gases other than hydrocarbons to the absorption of said first laser beam, determining the absorption of said first laser beam by said hydrocarbons and means for determining therefrom the hydrocarbon content in said sample.

* * * * *